(12) United States Patent  (10) Patent No.: US 8,837,096 B2
Seebruch  (45) Date of Patent: Sep. 16, 2014

(54) FAULT MONITOR FOR FAULT TOLERANT IMPLANTABLE PUMP

(75) Inventor: Craig H. Seebruch, Odessa, FL (US)

(73) Assignee: Thoratec Corporation, Pleasanton, CA (US)

( * ) Notice: Subject to any disclaimer, the term of this patent is extended or adjusted under 35 U.S.C. 154(b) by 365 days.

(21) Appl. No.: 13/418,447

(22) Filed: Mar. 13, 2012

(65) Prior Publication Data

US 2013/0245614 A1    Sep. 19, 2013

(51) Int. Cl.
*F21V 7/04*    (2006.01)

(52) U.S. Cl.
USPC .............................................. 361/23; 361/31

(58) Field of Classification Search
USPC ................................................ 361/23, 31, 87
See application file for complete search history.

(56) References Cited

U.S. PATENT DOCUMENTS

| | | | |
|---|---|---|---|
| 5,613,935 | A | 3/1997 | Jarvik |
| 6,149,683 | A | 11/2000 | Lancisi et al. |
| 6,320,731 | B1 | 11/2001 | Eaves et al. |
| 6,351,048 | B1 | 2/2002 | Schob et al. |
| 6,605,032 | B2 | 8/2003 | Benkowski et al. |
| 7,660,635 | B1 | 2/2010 | Verness et al. |
| 8,421,388 | B2 * | 4/2013 | Mukai ................ 318/400.21 |
| 8,545,381 | B2 * | 10/2013 | Kanebako ................ 600/16 |
| 2004/0145337 | A1 | 7/2004 | Morishita |
| 2005/0073273 | A1 | 4/2005 | Maslov et al. |
| 2008/0007196 | A1 | 1/2008 | Tan et al. |
| 2008/0211439 | A1 | 9/2008 | Yokota et al. |
| 2010/0305692 | A1 | 12/2010 | Thomas et al. |
| 2011/0015732 | A1 | 1/2011 | Kanebako |
| 2011/0218383 | A1 | 9/2011 | Broen et al. |
| 2011/0218384 | A1 | 9/2011 | Bachman et al. |
| 2011/0218385 | A1 | 9/2011 | Bolyard et al. |

FOREIGN PATENT DOCUMENTS

WO    9414226    6/1994

* cited by examiner

*Primary Examiner* — Danny Nguyen
(74) *Attorney, Agent, or Firm* — Kilpatrick Townsend & Stockton LLP

(57) ABSTRACT

A implantable pump system comprises an implantable pump motor and an external unit. An inverter comprises respective phases with redundant legs connected in parallel, and respective current sensors in series with each leg generating a respective measured current. A cable redundantly couples the inverter to the motor. The cable includes a respective conductor coupling each redundant leg to a respective phase of the motor. The controller receives the measured currents, monitors for a fault in the conductors by comparing the measured currents in the respective redundant legs. A fault in a pair of redundant conductors is detected if a ratio of the respective measured currents is not within a predetermined range.

6 Claims, 3 Drawing Sheets

FAULT MONITOR FOR FAULT TOLERANT IMPLANTABLE PUMP

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to circulatory assist devices, and, more specifically, to enhanced reliability and fault monitoring of cabling that connects an external unit to an implantable pump unit.

Many types of circulatory assist devices are available for either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. One such system is the DuraHeart® LVAS system made by Terumo Heart, Inc., of Ann Arbor, Mich. One embodiment of the DuraHeart® system may employ a centrifugal pump with a magnetically levitated impeller to pump blood from the left ventricle to the aorta. An electric motor magnetically coupled to the impeller is driven at a speed appropriate to obtain the desired blood flow through the pump.

A typical cardiac assist system includes a pumping unit, electrical motor (e.g., a brushless DC motor integrated into the pump), drive electronics, microprocessor control unit, and an energy source such as rechargeable batteries. The system may be implantable, either fully or partially. The goal of the control unit is to autonomously control the pump performance to satisfy the physiologic needs of the patient while maintaining safe and reliable system operation. A control system for varying pump speed to achieve a target blood flow based on physiologic conditions is shown in U.S. Pat. No. 7,160,243, issued Jan. 9, 2007, which is incorporated herein by reference in its entirety. Thus, a target blood flow rate may be established based on the patient's heart rate so that the physiologic demand is met. The control unit may establish a speed setpoint for the pump motor to achieve the target flow. Whether the control unit controls the speed setpoint in order to achieve flow on demand or whether a pump speed is merely controlled to achieve a static flow or speed as determined separately by a physician, it is essential to automatically monitor pump performance to ensure that life support functions are maintained.

A typical pump motor employed for a blood pump is a three-phase permanent magnet electric motor that can be driven as a brushless DC or a synchronous AC motor without any position sensor. The need for a position sensor is avoided by controlling motor operation with one of a variety of methods that use the measured stator phase currents to infer the position. Vector control is one typical method used in variable frequency drives to control the torque and speed of a three-phase electric motor by controlling the current fed to the motor phases. This control can be implemented using a fixed or variable voltage drive delivered via an inverter comprised of pulse width modulated H-bridge power switches arranged in phase legs. Reliability, fault detection, and fault tolerance are important characteristics of an electrically-powered blood pump, drive system, and cable, and it would be desirable to improve each of them.

SUMMARY OF THE INVENTION

In one aspect of the invention, a pump system comprises an implantable pump unit having a multiphase brushless motor and an external unit including a controller and an H-bridge inverter. The H-bridge inverter comprises a first phase with first and second redundant legs connected in parallel, a first current sensor in series with the first leg generating a first measured current, a second current sensor in series with the second leg generating a second measured current, a second phase with third and fourth redundant legs connected in parallel, a third current sensor in series with the third leg generating a third measured current, and a fourth current sensor in series with the fourth leg generating a fourth measured current. A cable redundantly couples the H-bridge inverter to the motor. The cable includes a first conductor coupling the first leg to a first respective phase of the motor, a second conductor coupling the second leg to the first respective phase of the motor, a third conductor coupling the third leg to a second respective phase of the motor, and a fourth conductor coupling the fourth leg to the second respective phase of the motor. The controller receives the measured currents, monitors for a fault in the first or second conductors by comparing the first and second measured currents, and monitors for a fault in the third or fourth conductors by comparing the third and fourth measured currents.

DETAILED DESCRIPTION OF PREFERRED EMBODIMENTS

Figures 1, 4:
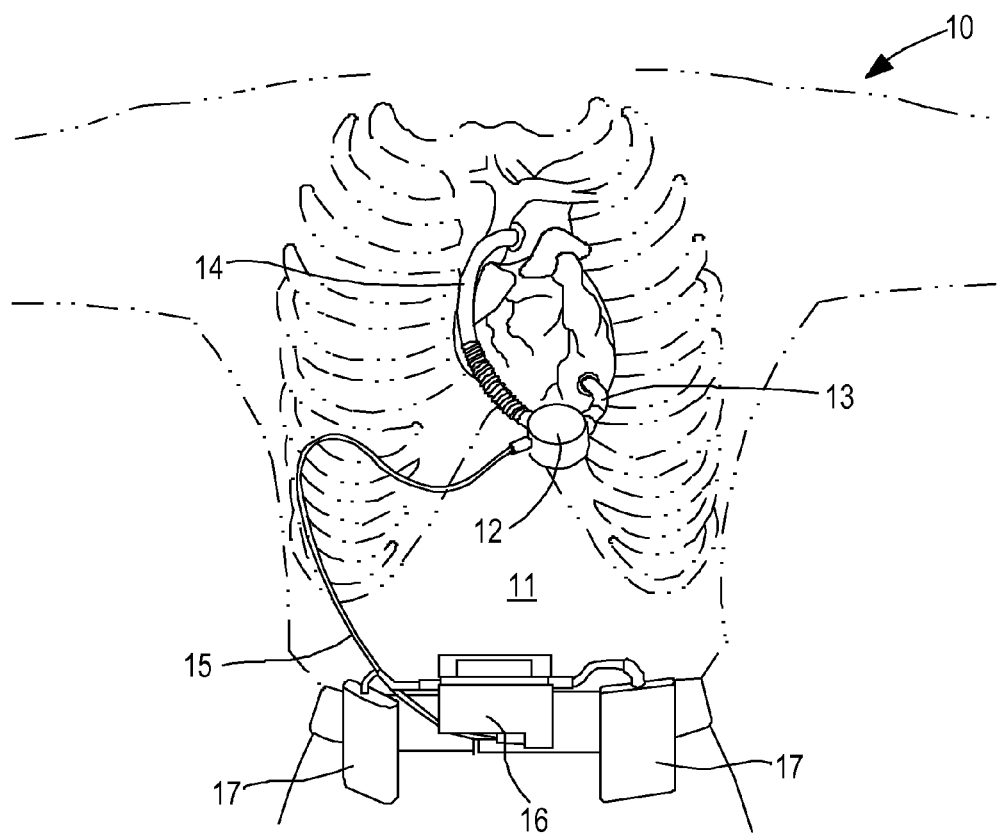
FIG. 1 is a diagram of a circulatory assist system as one example of an implantable pump employing the present invention.
FIG. 4 is a logic diagram showing a preferred embodiment of fault monitoring of the present invention.

Referring to FIG. 1, a patient 10 is shown in fragmentary front elevational view. Surgically implanted either into the patient's abdominal cavity or pericardium 11 is the pumping unit 12 of a ventricular assist device. An inflow conduit 13 conveys blood from the patient's left ventricle into pumping unit 12, and an outflow conduit 14 conveys blood from pumping unit 12 to the patient's ascending thoracic aorta. A power cable 15 extends from pumping unit 12 outwardly of the patient's body via an incision to a compact controller 16. A power source, such as a battery pack 17 worn on a belt about the patient's waist, is connected with controller 16.

Cable 15 is flexible in order to allow freedom of movement of the patient. Such movement, however, causes stresses to cable 15 and to its connections with pumping unit 12 and controller 16. To increase reliability and fault tolerance, the present invention uses redundant conductors in cable 15 to supply each of the phase currents that drive the pump motor.

Figure 2:
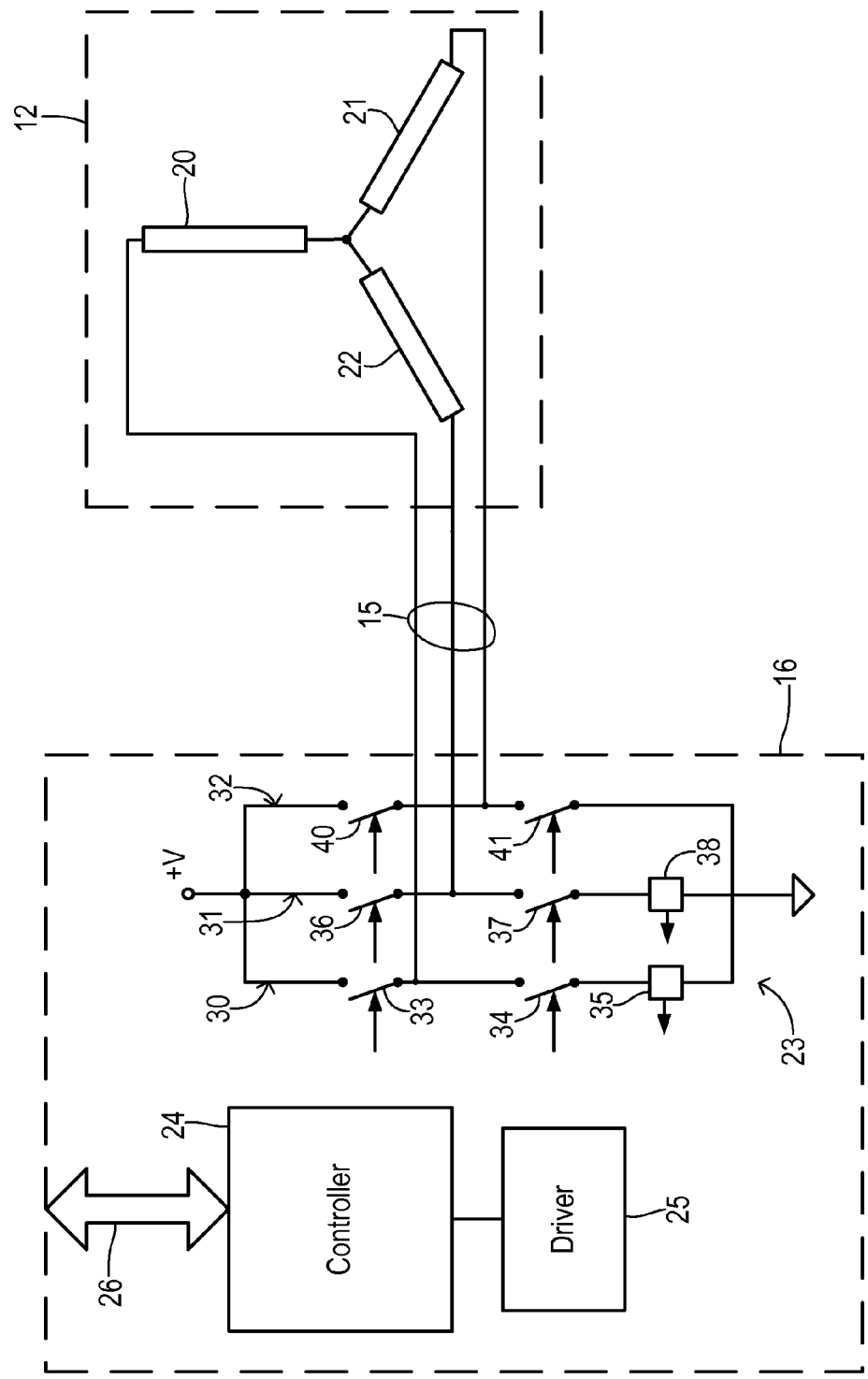
FIG. 2 is a schematic diagram showing a conventional ventricular assist system employing an H-bridge inverter.

A conventional inverter and cabling for an LVAD system is shown in FIG. 2. A DC motor in pump unit 12 has phases 20-22 connected by cable 15 to an H-bridge inverter 23. A controller 24, such as a general purpose microcontroller, implements a vector control or other algorithm to determine proper energization of phases 20-22 to obtain the desired motor operation. Controller 24 is connected to a driver 25 for generating drive signals coupled to the control inputs of individual switches (e.g., transistors) in inverter 23. Controller 24 has an input/output 26 for sending messages or generating fault alarms directed at the user or a physician, for example.

Inverter 23 has an H-bridge configuration with a first phase leg 30, a second phase leg 31, and a third phase leg 32. Phase leg 30 has an upper switch 33 and a lower switch 34 which are turned on and off by controller 24 via driver 25 as known in the art. A current sensor 35 in series with phase leg 30 provides a measured current to controller 24 as an input to the vector control algorithm. Similarly, phase leg 31 includes switches 36 and 37 and a current sensor 38. Phase leg 32 includes switches 40 and 41, but a current sensor may not be required since the vector control algorithm can infer a third current based on measured currents from sensors 35 and 38.

Figure 3:
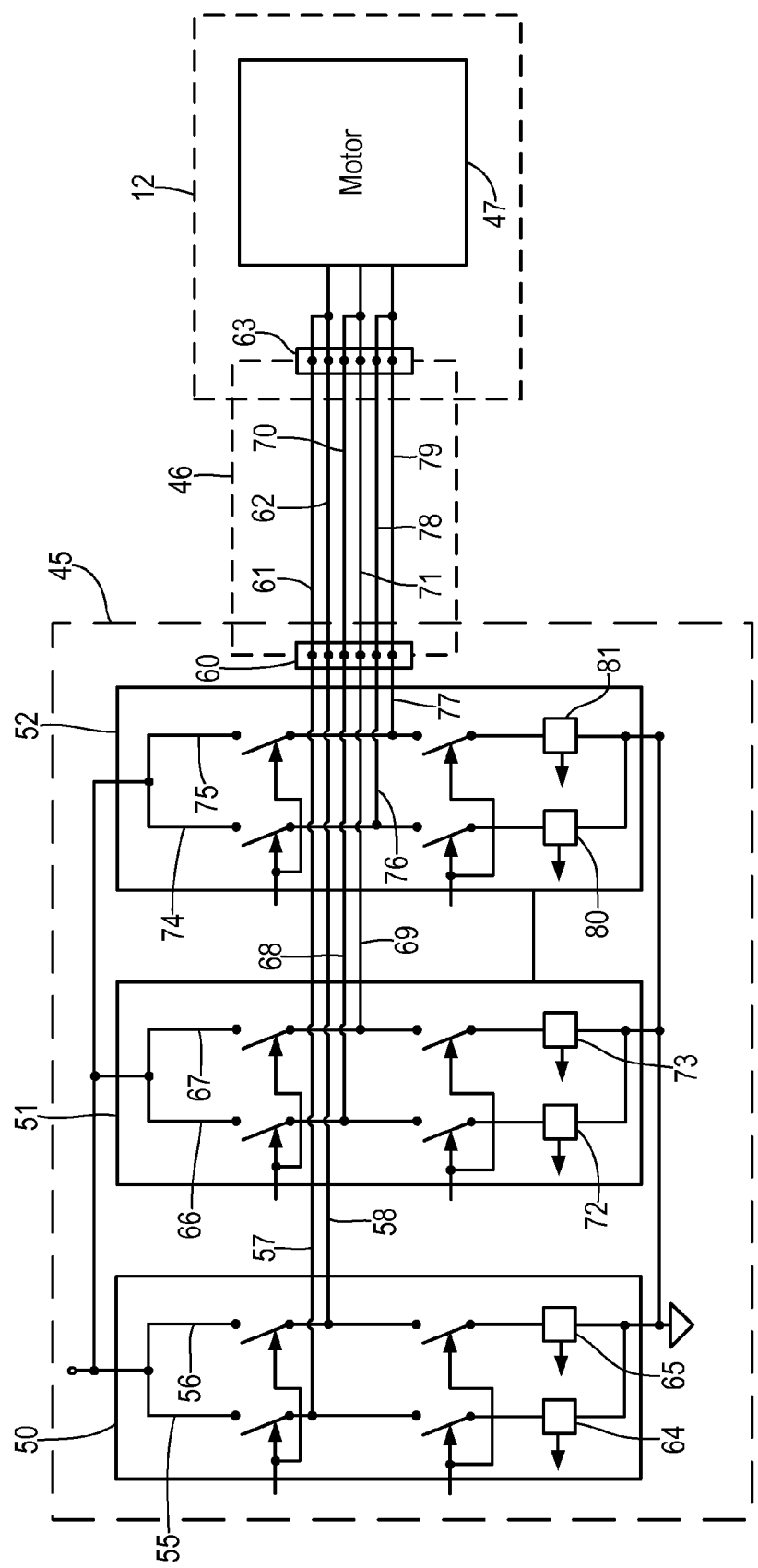
FIG. 3 is a schematic diagram showing redundant phase legs and cable conductors employed in one embodiment of the present invention.

FIG. 3 shows an improved ventricular assist system having higher reliability and fault tolerance as a result of redundant cable conductors and redundant phase legs. Thus, an inverter 45 is coupled by a redundant cable 46 to motor 47 in pump unit 12. Inverter 45 has a first phase 50, a second phase 51, and a third phase 52. First phase 50 has a first phase leg 55 and a second phase leg 56. The upper and lower power switches in legs 55 and 56 are respectively coupled together to provide synchronous operation of the legs. Respective conductors 57 and 58 connect phase legs 55 and 56 to a connector terminal 60. Cable 46 includes conductors 61 and 62 connected at terminal 60 to conductors 57 and 58, respectively. Conductors 61 and 62 are coupled to motor 47 via a terminal connector 63 in pump unit 12. Redundant conductors 61 and 62 become interconnected within pump unit 12 in order to drive a respective phase of motor 47.

Legs 55 and 56 include respective current sensors 64 and 65 measuring the separate current magnitudes flowing in each of legs 55 and 56. The measured currents are coupled to the controller for monitoring and motor control purposes as explained below.

Phases 51 and 52 of inverter 45 have an identical configuration. Thus, phase 51 includes redundant phase legs 66 and 67, which are independently connected to terminal 60 by conductors 68 and 69. Corresponding conductors 70 and 71 are provided in cable 46. Current sensors 72 and 73 provide measured currents for phase leg 66 and 67 to the controller. Phase 52 includes legs 74 and 75 having their outputs connected to terminal 60 by conductors 76 and 77. Cable 46 includes conductors 78 and 79 which connect conductors 76 and 77 to pump unit terminal 63. Phase 52 includes current sensors 80 and 81 in legs 74 and 75, respectively, which provide measured currents for legs 74 and 75 to the controller.

The redundancy of the cable conductors, phase leg switches, and phase leg conductors provide fault tolerance whereby damage such as loss of continuity in one conductor or failure of one switch does not prevent operation of the ventricle assist system. Upon failure of one of these, the redundant conductor or phase leg carries the full current load instead of being distributed between the redundant elements, thereby providing continuous operation of the pump.

Fault monitoring is performed by comparing measured currents within redundant phase legs. Specifically, if the currents are substantially equal (indicating that operation of electrical components is the same in each redundant leg) then conditions are nominal and no fault is detected. If the measured currents are substantially unequal, on the other hand, then a fault is detected. The fault occurrence may trigger an alarm to inform a user that steps should be taken to remedy the fault. However, regular pump operation is maintained by virtue of the redundant element continuing to supply the proper current to the motor.

In a preferred embodiment, measured currents from redundant legs of the same phase are compared by forming a ratio of the measured currents. Assuming no fault is present, then the currents are about equal and the ratio has a value near 1. Thus, the ratio may be compared to a range centered on 1 (e.g., from 0.8 to 1.2) such that no fault is present when the ratio is within the range, and a fault is detected when the ratio falls outside the range. In controlling the motor based on the phase currents, the controller sums the two measured currents from the redundant legs corresponding to each phase and uses each summed current as an input to the vector control algorithm. Thus, the present invention does not necessitate any changes in the motor control algorithm itself. However, it may be possible to simplify the algorithm since the invention provides actual measurements of the currents in all three phases instead of just two.

The controller may preferably perform fault monitoring using the logic shown in FIG. 4. Respective phase currents $i_{A1}$ and $i_{A2}$ from current sensors in the respective phase legs of a single phase A may be converted to digital values in analog-to-digital converters 85 and 86. A ratio block 87 determines the ratio of the currents which is then provided to inputs of comparators 88 and 89. Comparator 88 compares the ratio with an upper threshold $T_1$ and generates a high-level logic output signal when the ratio is greater than $T_1$. Comparator 89 compares the ratio with a lower threshold $T_2$. When the ratio is below threshold $T_2$, then a low-level logic output is generated by comparator 89. An OR-gate 90 has its inputs coupled to the respective outputs of comparators 88 and 89, whereby when the ratio is outside the range defined by thresholds $T_1$ and $T_2$, then a high-level logic signal is provided at output 91 of OR-gate 90. In response to the detected fault, the controller may preferably generate an alarm to signify the need to take corrective action.

What is claimed is:

1. A pump system comprising:
    an implantable pump unit having a multiphase brushless motor;
    an external unit including a controller and an H-bridge inverter, wherein the H-bridge inverter comprises:
        a first phase with first and second redundant legs connected in parallel;
        a first current sensor in series with the first leg generating a first measured current;
        a second current sensor in series with the second leg generating a second measured current;
        a second phase with third and fourth redundant legs connected in parallel;
        a third current sensor in series with the third leg generating a third measured current; and
        a fourth current sensor in series with the fourth leg generating
    a fourth measured current; and
    a cable redundantly coupling the H-bridge inverter to the motor, wherein the cable includes a first conductor coupling the first leg to a first respective phase of the motor, a second conductor coupling the second leg to the first respective phase of the motor, a third conductor coupling the third leg to a second respective phase of the motor, and a fourth conductor coupling the fourth leg to the second respective phase of the motor;

wherein the controller receives the measured currents, monitors for a fault in the first or second conductors by comparing the first and second measured currents, and monitors for a fault in the third or fourth conductors by comparing the third and fourth measured currents.

2. The system of claim 1 wherein the controller sums the first and second measured currents to provide a first phase current, sums the third and fourth measured currents to provide a second phase current, and controls operation of the H-bridge inverter in response to the phase currents.

3. The system of claim 1 wherein the first and second measured currents are compared by forming a first ratio of the first and second measured currents, the fault in the first or second conductors being detected if the first ratio is not within a predetermined range.

4. The system of claim 3 wherein the third and fourth measured currents are compared by forming a second ratio of the third and fourth measured currents, the fault in the third or fourth conductors being detected if the second ratio is not within the predetermined range.

5. The system of claim 1 wherein the H-bridge inverter further comprises a third phase with fifth and sixth redundant legs, a fifth current sensor in series with the fifth leg generating a fifth measured current, and a sixth current sensor in series with the sixth leg generating a sixth measured current;

wherein the cable further includes a fifth conductor coupling the fifth leg to a third respective phase of the motor, and a sixth conductor coupling the sixth leg to the third respective phase of the motor; and wherein the controller monitors for a fault in the fifth or sixth conductors by comparing the fifth and sixth measured currents.

6. The system of claim 5 wherein the measured currents of each respective phase are compared by forming a respective ratio of the respective measured currents, the fault in the respective conductors for a respective phase being detected if the respective ratio is not within a predetermined range.

* * * * *